United States Patent
Schmoll et al.

(10) Patent No.: US 9,778,018 B2
(45) Date of Patent: Oct. 3, 2017

(54) SWEPT SOURCE INTERFEROMETRIC IMAGING SYSTEMS AND METHODS

(71) Applicant: Carl Zeiss Meditec, Inc., Dublin, CA (US)

(72) Inventors: Tilman Schmoll, Dublin, CA (US); Matthew J. Everett, Livermore, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 57 days.

(21) Appl. No.: 14/613,121

(22) Filed: Feb. 3, 2015

(65) Prior Publication Data

US 2015/0233700 A1 Aug. 20, 2015

Related U.S. Application Data

(60) Provisional application No. 61/939,838, filed on Feb. 14, 2014.

(51) Int. Cl.
*G01B 9/02* (2006.01)
*A61B 3/10* (2006.01)

(52) U.S. Cl.
CPC .......... *G01B 9/02004* (2013.01); *A61B 3/102* (2013.01); *G01B 9/02005* (2013.01); *G01B 9/02077* (2013.01); *G01B 9/02091* (2013.01)

(58) Field of Classification Search
CPC ............ G01B 9/02004; G01B 9/02005; G01B 9/02077; G01B 9/02091; G01B 9/0209; A61B 3/102
USPC ................................. 356/479, 497
See application file for complete search history.

(56) References Cited

U.S. PATENT DOCUMENTS

| | | | |
|---|---|---|---|
| 6,549,801 B1 | 4/2003 | Chen et al. | |
| 6,738,144 B1* | 5/2004 | Dogariu | G01N 15/0211 356/335 |
| 7,732,784 B2 | 6/2010 | Shimizu et al. | |
| 8,873,066 B2 | 10/2014 | Ensher et al. | |
| 2005/0171438 A1 | 8/2005 | Chen et al. | |
| 2010/0027020 A1* | 2/2010 | Nebosis | A61B 5/0066 356/450 |
| 2010/0027857 A1* | 2/2010 | Wang | A61B 3/102 382/128 |

(Continued)

FOREIGN PATENT DOCUMENTS

WO 2014/023770 A2 2/2014

OTHER PUBLICATIONS

Bonesi et al., "Akinetic All-Semiconductor Programmable Swept-Source At 1550 nm and 1310 nm With Centimeters Coherence Length", Optics Express, vol. 22, No. 3, Feb. 10, 2014, pp. 2632-2655.

(Continued)

*Primary Examiner* — Tarifur Chowdhury
*Assistant Examiner* — Jonathon Cook
(74) *Attorney, Agent, or Firm* — Morrison & Foerster LLP (57) ABSTRACT

Embodiments herein include swept-source interferometric imaging systems employing arbitrary sweep patterns in which a swept-source is swept over a continuous spectral range where the variation of wavelength over time is non-continuous. Embodiments include sweep patterns that result in reduction of signals from moving scatterers and where the sweep is synchronized with the dead time of the camera.

9 Claims, 7 Drawing Sheets

(56) References Cited

U.S. PATENT DOCUMENTS

| | | | |
|---|---|---|---|
| 2010/0157311 A1* | 6/2010 | Hayashi | G01N 21/4795 356/496 |
| 2012/0277579 A1 | 11/2012 | Sharma et al. | |
| 2012/0307014 A1 | 12/2012 | Wang | |
| 2013/0278935 A1* | 10/2013 | Yamada | G01B 9/02004 356/479 |
| 2013/0301000 A1 | 11/2013 | Sharma et al. | |
| 2014/0028974 A1 | 1/2014 | Tumlinson | |
| 2014/0368827 A1 | 12/2014 | Fujii | |

OTHER PUBLICATIONS

Bonin et al., "In Vivo Fourier-Domain Full-Field OCT of the Human Retina with 1.5 Million A-lines/s", Optics Letters, vol. 35, No. 20, Oct. 12, 2010, pp. 3432-3434.

Choi et al., "Tuning of Successively Scanned Two Monolithic Vernier-Tuned Lasers and Selective Data Sampling in Optical Comb Swept Source Optical Coherence Tomography", Biomedical Optics Express, vol. 4, No. 12, Dec. 1, 2013, pp. 2962-2987.

Choma et al., "Sensitivity Advantage of Swept Source and Fourier Domain Optical Coherence Tomography", Optics Express, vol. 11, No. 18, Sep. 8, 2003, pp. 2183-2189.

George et al., "High-Speed Concatenation of Frequency Ramps Using Sampled Grating Distributed Bragg Reflector Laser Diode Sources for OCT Resolution Enhancement", Proc. of SPIE, vol. 7554, 2010, pp. 75542O-1-75542O-8.

Hendargo et al., "Doppler Velocity Detection Limitations in Spectrometer-Based Versus Swept-Source Optical Coherence Tomography", Biomedical Optics Express, vol. 2, No. 8, Aug. 1, 2011, pp. 2175-2188.

Hillmann et al., "Efficient Holoscopy Image Reconstruction", Optics Express, vol. 20, No. 19, Sep. 10, 2012, pp. 21247-21263.

Hillmann et al., "Holoscopy—Holographic Optical Coherence Tomography", Optics Letters, vol. 36, No. 13, Jul. 1, 2011, pp. 2390-2392.

Huang et al., "Optical Coherence Tomography", Science, vol. 254, Nov. 22, 1991, pp. 1178-1181.

Ishii et al., "Mode Stabilization Method for Superstructure-Grating DBR Lasers", Journal of Lightwave Technology, vol. 16, No. 3, Mar. 1998, pp. 433-442.

Ishii et al., "Quasicontinuous Wavelength Tuning in Super-Structure-Grating (SSG) DBR Lasers", IEEE Journal of Quantum Electronics, vol. 32, No. 3, Mar. 1996, pp. 433-441.

Jia et al., "Split-Spectrum Amplitude-Decorrelation Angiography with Optical Coherence Tomography", Optics Express, vol. 20, No. 4, Feb. 13, 2012, pp. 4710-4725.

Kim, M. K., "Tomographic Three-Dimensional Imaging of a Biological Specimen Using Wavelength-Scanning Digital Interference Holography", Optics Express, vol. 7, No. 9, Oct. 23, 2000, pp. 305-310.

Lee et al., "In vivo Optical Frequency Domain Imaging of Human Retina and Choroid", Optics Express, vol. 14, No. 10, May 15, 2006, pp. 4403-4411.

Lee et al., "Line-Field Optical Coherence Tomography Using Frequency-Sweeping Source", IEEE Journal of Selected Topics in Quantum Electronics, vol. 14, No. 1, Jan./Feb. 2008, pp. 50-55.

Leitgeb et al., "Performance of Fourier Domain vs. Time Domain Optical Coherence Tomography", Optics Express vol. 11, No. 8, Apr. 21, 2003, pp. 889-894.

Leitgeb et al., "Ultrahigh Resolution Fourier Domain Optical Coherence Tomography", Optics Express, vol. 12, No. 10, May 17, 2004, pp. 2156-2165.

Minneman et al., "All-Semiconductor High-Speed Akinetic Swept-Source for OCT", SPIE-OSA-IEEE, vol. 8311, 2011, pp. 831116-1-831116-10.

Mujat et al., "Swept-Source Parallel OCT", Proc. of SPIE, vol. 7168, 2009, pp. 71681E-1-71681E-8.

Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.

Považay et al., "Full-Field Time-Encoded Frequency-Domain Optical Coherence Tomography", Optics Express, vol. 14, No. 17, Aug. 21, 2006, pp. 7661-7669.

Ralston et al., "Interferometric Synthetic Aperture Microscopy", Nature Physics, vol. 3, Feb. 2007, pp. 129-134.

Tokayer et al., "Blood Flow Velocity Quantification Using Splitspectrum Amplitude-Decorrelation Angiography with Optical Coherence Tomography", Biomedical Optics Express, vol. 4, No. 10, Oct. 1, 2013, pp. 1909-1924.

Wojtkowski et al., "Three-dimensional Retinal Imaging with High-Speed Ultrahigh-Resolution Optical Coherence Tomography", Ophthalmology, vol. 112, No. 10, Oct. 2005, pp. 1734-1746.

Yun et al., "Pulsed-Source and Swept-Source Spectral-Domain Optical Coherence Tomography with Reduced Motion Artifacts", Optics Express, vol. 12, No. 23, Nov. 15, 2004, pp. 5614-5624.

* cited by examiner

SWEPT SOURCE INTERFEROMETRIC IMAGING SYSTEMS AND METHODS

PRIORITY

The present application claims priority to U.S. Provisional Application Ser. No. 61/939,838 filed Feb. 14, 2014 and hereby incorporated by reference in its entirety.

TECHNICAL FIELD

The present application relates to the field of interferometric imaging, in particular to the sweeping patterns used in swept-source interferometric imaging systems.

BACKGROUND

A wide variety of interferometric imaging techniques have been developed to provide high resolution structural information in a wide range of applications. Optical Coherence Tomography (OCT) is a technique for performing high-resolution cross-sectional imaging that can provide images of samples including tissue structure on the micron scale in situ and in real time (Huang et al., 1991). OCT is an interferometric imaging method that determines the scattering profile of a sample along the OCT beam by detecting light reflected from a sample combined with a reference beam. Each scattering profile in the depth direction (z) is called an axial scan, or A-scan. Cross-sectional images (B-scans), and by extension 3D volumes, are built up from many A-scans, with the OCT beam moved to a set of transverse (x and y) locations on the sample.

Many variants of OCT have been developed where different combinations of light sources, scanning configurations, and detection schemes are employed. In time domain OCT (TD-OCT), the path length between light returning from the sample and reference light is translated longitudinally in time to recover the depth information in the sample. In frequency domain or Fourier domain OCT (FD-OCT), the broadband interference between reflected sample light and reference light is acquired in the spectral domain and a Fourier transform is used to recover the depth information. The sensitivity advantage of frequency-domain optical coherence tomography (OCT) over time-domain OCT is well established (Choma, Sarunic, Yang, & Izatt, 2003; Leitgeb, Hitzenberger, & Fercher, 2003).

There are two common approaches to FD-OCT. One is spectral domain OCT (SD-OCT) where the interfering light is spectrally dispersed prior to detection and the full depth information can be recovered from a single exposure. The second is swept-source OCT (SS-OCT) where the source is swept over a range of frequencies and detected over time, therefore encoding the spectral information in the time dimension. In traditional point scanning or flying spot techniques, a single point of light is scanned across the sample. In parallel techniques, a series of spots, a line of light (line-field), or a two-dimensional array of light (full-field or partial field) are directed to the sample. The resulting reflected light is combined with reference light and detected. Parallel techniques can be accomplished in TD-OCT, SD-OCT or SS-OCT configurations. (Lee & Kim, 2008; Mujat, Iftimia, Ferguson, & Hammer, 2009; Nakamura et al., 2007)

The related fields of optical diffraction tomography, holoscopy, digital interference holography, holographic OCT, and interferometric synthetic aperture microscopy (Hillman, Luhrs, Bonin, Koch, & Huttmann, 2011; Kim, 2000; Ralston, Marks, Scott Carney, & Boppart, 2007) are also interferometric imaging techniques that can be accomplished in parallel and in particular line-field scanning configurations (see for example U.S. patent application Ser. No. 13/745,632 hereby incorporated by reference).

Interferometric imaging with swept sources may suffer from motion artifacts caused by axial motion of scatterers. An axial moving scatterer can cause three different artifacts, axial point spread function (PSF) broadening, transverse PSF broadening as well as an axial shift. The axial shift, caused by a Doppler shift proportional to the axial velocity of the moving scatterer, may be the most critical of the three. Especially when imaging the human eye at relatively low sweep rates, the signal from the blood inside the retinal blood vessels may appear to be shifted up or down within the image. This may cause significant confusion among operators and could potentially lead to misdiagnosis. It is therefore desirable to develop systems and methods for attenuating the signal of moving scatterers in swept-source interferometric imaging techniques.

SUMMARY

Swept or tunable light sources used for interferometric imaging currently sweep the wavelength over a continuous spectral range typically either from short to long wavelengths or vice versa. Here we describe arbitrary sweep patterns in which the source is swept over a continuous spectral range where the variation of wavelength over time is noncontinuous. The laser could be swept in different "directions" throughout a sweep or different parts of the spectrum could be swept out of spectral order at different times in the sweep. In so doing, one may generate an interferometric fringe signal which is phase stable for static scatterers but phase instable for moving scatterers. The phase instability may in certain cases be desirable. It causes the signal from the moving scatterers to spread out and therefore be attenuated. Depending on the degree of the created phase discontinuities, the signal may spread so far that it appears in the final image only as an increase in the overall noise floor. Embodiments where the sweep is synchronized with the dead time of the camera are also presented.

DETAILED DESCRIPTION

Figure 1:
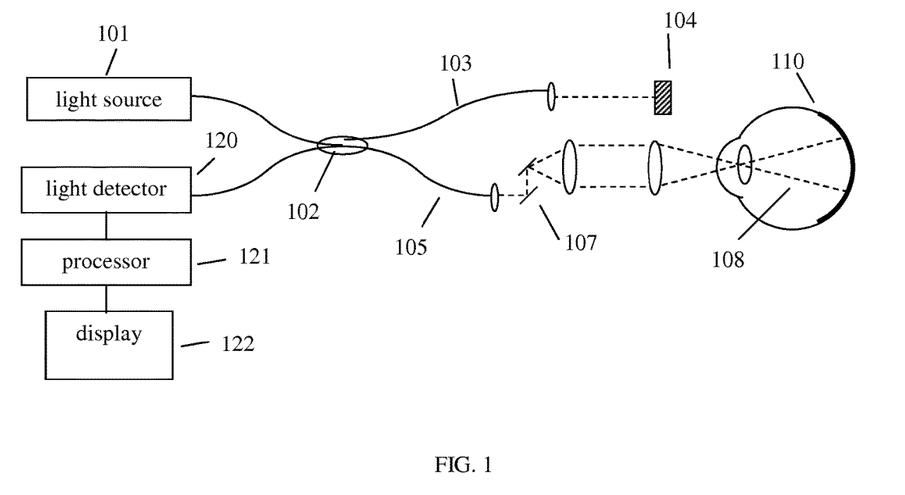
FIG. 1 illustrates a typical point scanning FD-OCT instrument that can be used with the custom sweep patterns of the present application.
Figure 2:
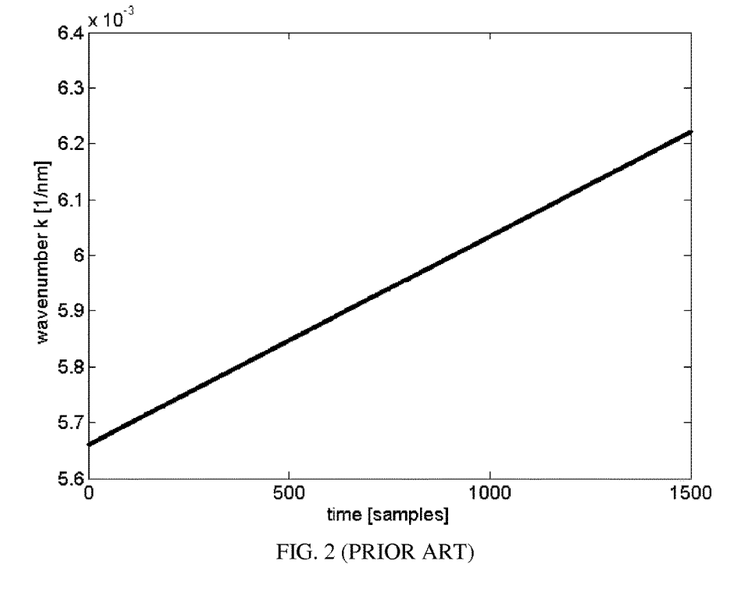
FIG. 2 illustrates a continuous sweep pattern that monotonically increases in wavenumber as is known in the prior art.

FIG. 1 illustrates the basic components of an optical coherence tomography system, one type of interferometric imaging system that could employ an arbitrary sweep pattern as described herein. The system includes a light source, 101, for the embodiments described herein, a swept laser source. (See for example, Wojtkowski, et al., "Three-dimensional retinal imaging with high-speed ultrahigh-resolution optical coherence tomography," *Ophthalmology* 112(10): 1734 2005 or Lee et al. "In vivo optical frequency domain imaging of human retina and choroid," *Optics Express* 14(10):4403 2006) Swept or tunable light sources used for interferometric imaging currently sweep the wavelength over a continuous spectral range typically either from short to long wavelengths or vice versa as illustrated in FIG. 2 where the spectral range is shown in wavenumbers (vertical axis) vs. time (horizontal axis).

Light from source 101 is routed, typically by optical fiber 105, to illuminate the sample 110, a typical sample being tissues at the back of the human eye. The light is scanned, typically with a scanner 107 between the output of the fiber and the sample, so that the beam of light (dashed line 108) is scanned over the area or volume to be imaged. Light scattered from the sample is collected, typically into the same fiber 105 used to route the light for illumination. Reference light derived from the same source 101 travels a separate path, in this case involving fiber 103 and retroreflector 104. Those skilled in the art recognize that a transmissive reference path can also be used. Collected sample light is combined with reference light, typically in a fiber coupler 102, to form light interference in a detector 120. The output from the detector is supplied to a processor 130. The results can be stored in the processor or displayed on display 140. The interferometer can contain bulk optics, fiber components or a combination of the two. For swept source systems, typically a balanced detector set-up is employed.

The interference causes the intensity of the interfered light to vary across the spectrum. For any scattering point in the sample, there will be a certain difference in the path length between light from the source and reflected from that point, and light from the source traveling the reference path. The interfered light has an intensity that is relatively high or low depending on whether the path length difference is an even or odd number of half-wavelengths, as these path length differences result in constructive or destructive interference respectively. Thus the intensity of the interfered light varies with wavelength in a way that reveals the path length difference; greater path length difference results in faster variation between constructive and destructive interference across the spectrum. The Fourier transform of the interference spectrum reveals the profile of scattering intensities at different path lengths, and therefore scattering as a function of depth in the sample (Leitgeb et al., 2004). The profile of scattering as a function of depth is called an axial scan (A-scan). A set of A-scans measured at neighboring locations in the sample produces a cross-sectional image (tomogram) of the sample.

Axial sample motion during a swept source interferometric measurement can cause three different image artifacts: axial point spread function (PSF) broadening, axial shift due to a Doppler shift and transverse PSF broadening. The severity of these artifacts is proportional to the axial velocity component of the moving sample as well as to the time to acquire one sweep. Therefore especially relatively slow sweeping swept source systems suffer more from such artifacts. Since the sweep time is increased in parallel interferometric techniques with swept sources, such as line field SS-OCT or full field SS-OCT, their images are particularly vulnerable to the above mentioned motion artifacts.

While an axial shift of an entire tomogram does not cause much concern, axial shifts of only parts of the tomogram could cause significant confusion for the operator. A common scenario where part of the sample is shifted, while another part remains at its original position within the tomogram, can be seen while imaging the human retina in-vivo. In the optic nerve head region, blood vessels enter and exit the inner retina at often relatively steep angles. In these areas the moving blood cells have a large axial velocity component, which can cause a significant Doppler shift. This Doppler shift can result in an axial position shift of the signal backscattered from the blood cells within the tomogram. Since the tissue surrounding the blood vessels remains fairly static within the time frame of one sweep, it does not cause the same Doppler shift. The blood vessels may therefore appear to be shifted up or down within the tomogram and may in severe cases even appear above or below the retinal structure. Such artifacts would certainly confuse the operator and may result in misdiagnosis.

In the prior art it was suggested to detect the axial velocity of the blood and use this information to reverse the axial shift numerically in post processing (Hendargo, McNabb, Dhalla, Shepherd, & Izatt, 2011). To detect the axial velocity, one commonly measures the same location twice and calculates the phase difference between the two successive measurements.

In some cases, for example when the image artifact should be suppressed in real time or when the phase shift between two successive measurements is very large, it may be desirable to simply suppress the signal from the moving particles at the time of acquisition. To accomplish this, it is described herein how to sweep the swept source instead of monotonically from short wavelength to long wavelength or vice versa, in an arbitrary sweep pattern.

Figure 3:
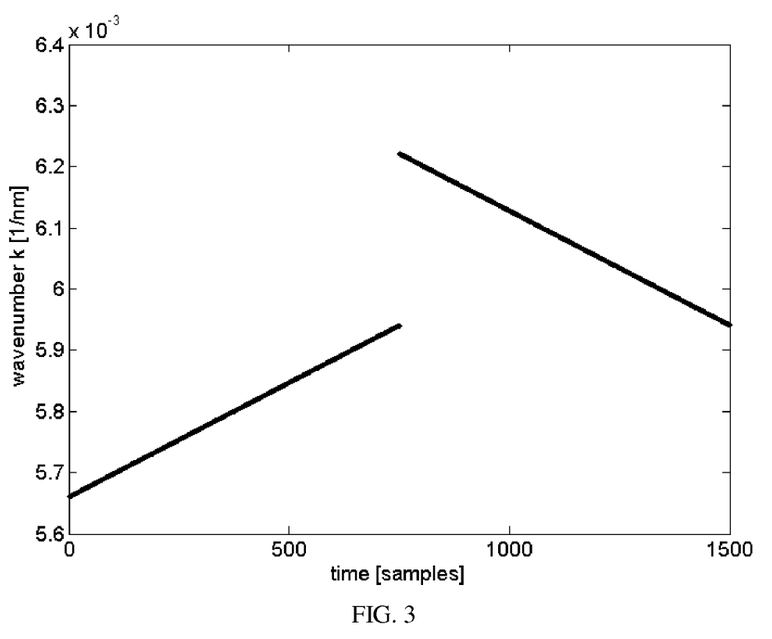
FIG. 3 shows a sweep pattern according to an embodiment of the present application where the sweep direction is changed mid-sweep from monotonically increasing in wavenumber to monotonically decreasing in wavenumber.
Figure 4:
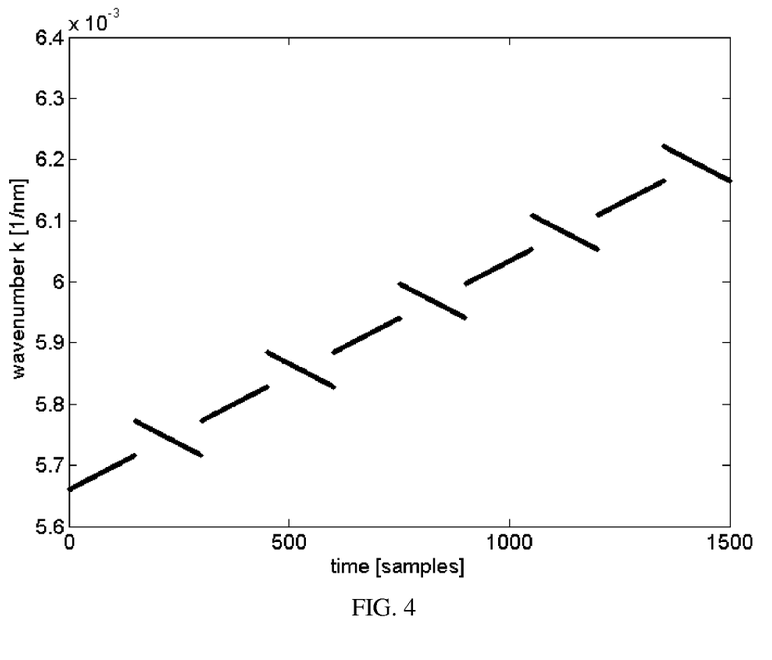
FIG. 4 illustrates a sweep pattern according to an embodiment of the present application where the sweep is broken into ten segments and the sweep direction is changed back and forth between increasing in wavenumber and decreasing in wavenumber.
Figure 5:
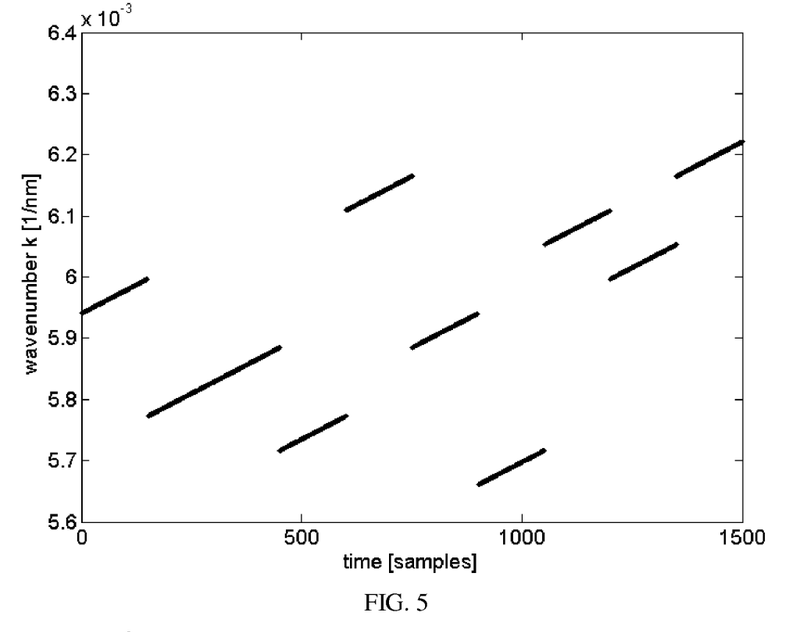
FIG. 5 illustrates a sweep pattern according to an embodiment of the present application where different wavenumber regions are output at different times of the sweep.
Figure 6:
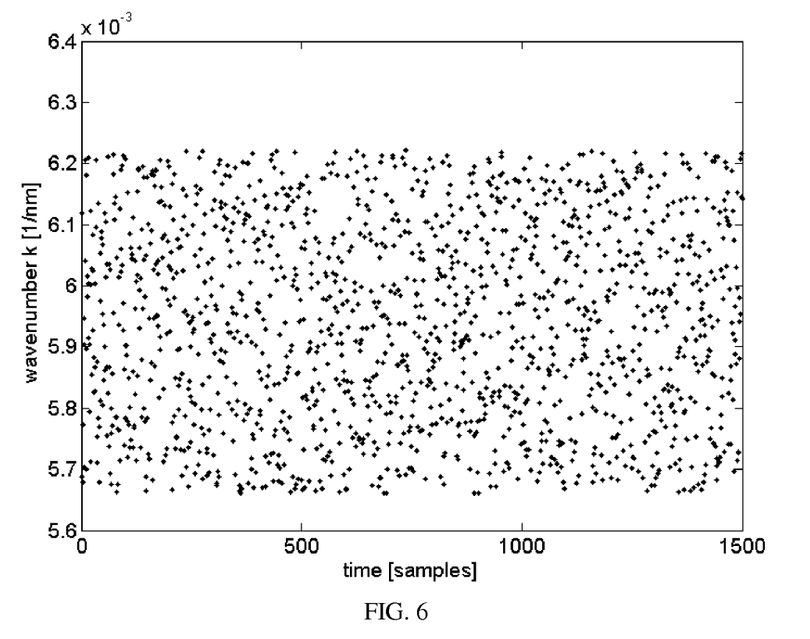
FIG. 6 illustrates an arbitrary sweep pattern according to the present application covering the range of wavenumbers shown in FIG. 1 but in a completely random order.

Some examples for arbitrary sweep patterns where the source is swept over a continuous wavelength or wavenumber range non-continuously in time are illustrated in FIGS. 3-6. All of these figures illustrate sweep patterns as wavenumber (x-axis) vs. time (y-axis). They could also be shown with wavelength as the x-axis. FIG. 3 shows a sweep pattern (wavenumber vs. time) where a portion of the sweep is swept in one sweep direction (direction in wavelength or wavenumber) and another portion of the sweep is swept in the opposite direction. The selection of two portions is arbitrary. FIG. 4 shows a sweep covering a continuous range of wavelengths where the sweep has been broken into a number of segments and the sweep direction (direction in wavelength or wavenumber) is alternated throughout the sweep. The number and length of segments is arbitrary. FIG. 5 illustrates an arbitrary sweep pattern where the full spectral range is swept by outputting different sections of the sweep in arbitrary order throughout the sweep period. 10 segments are shown in this figure but the sweep could be divided into an arbitrary number of segments of equal or unequal lengths. A final example of an arbitrary sweep pattern is shown in FIG. 6 where the full sweep range of the source is achieved by outputting different wavelength values in an arbitrary order throughout the sweep period.

Such sweep modes would still allow imaging of static samples without a loss in image quality. However, as soon as a phase shift over time is introduced in either the sample or reference arm, e.g. by axial motion of the sample, the phase of the moving scatterer's fringe signal will get distorted. As a result of this phase distortion, the signal from the moving scatterer appears broadened in a tomogram. Depending on the degree of the created phase discontinuities, the signal may spread so far that it appears in the final image only as an increase in the noise floor.

Many swept sources used for interferometric imaging can only sweep continuously from either a short wavelength to a long wavelength or from a long wavelength to a short wavelength (FIG. 1). "Arbitrary sweeps" are often not supported due to the swept source's mechanical sweep mechanisms. For example, changing the direction of movement of the MEMS mirror of a MEMS based external cavity tunable laser (ECTL) mid-sweep may be very challenging and could cause significant performance degradation due to the inertia of the mirror. There are however also swept source designs which are well suited for such operation modes. In particular akinetic lasers with no moving parts like semiconductor tunable lasers, such as SG-DBR, SSG-DBR, VT-DBR lasers, swept sources employing acousto optical tunable filters or swept sources employing electro optical deflectors for their sweep mechanism, to only name a few examples. (Bonesi et al., 2014; Choi, Yoshimura, & Ohbayashi, 2013; George & Derickson, 2010; Ishii, Kano, Yoshikuni, & Yasaka, 1998; Ishii et al., 1996; Minneman, Ensher, Crawford, & Derickson, 2011)

Also the increased sweep time of parallel interferometric imaging systems makes it only more feasible to change the sweep direction, sweep trajectory, sweep speed, optical power, polarization or the phase throughout the sweep.

Figure 7:
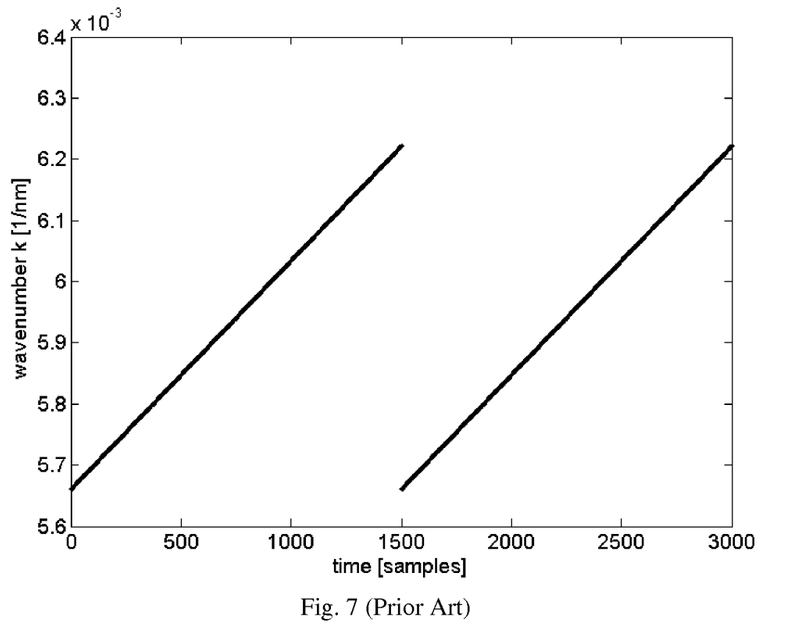
FIG. 7 illustrates a sweep pattern for a pair of repeat continuous sweeps where each sweep increases in wavenumber monotonically as is known in the prior art.
Figure 8:
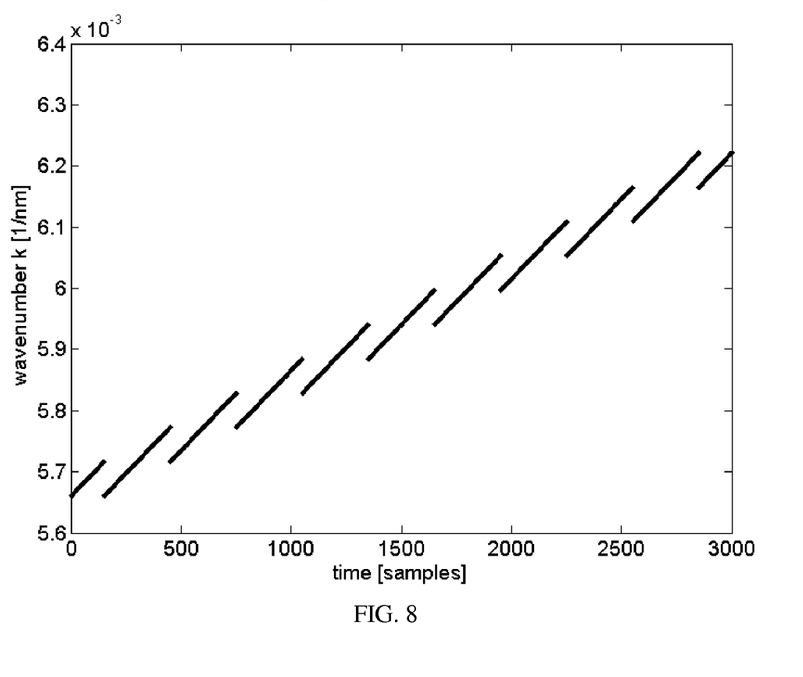
FIG. 8 shows a sweep pattern according to one embodiment of the present application in which a pair of repeat sweeps is achieved by interleaving.
Figure 9:
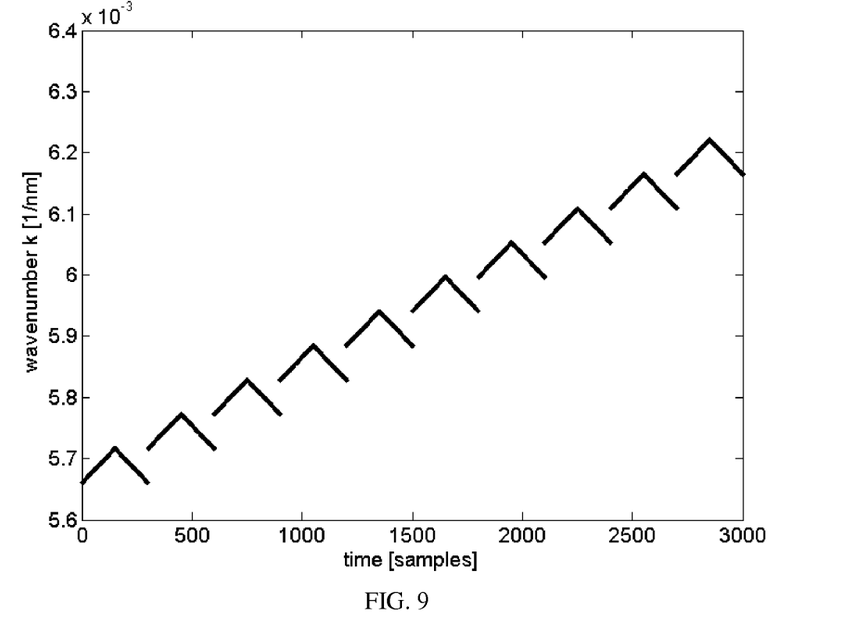
FIG. 9 illustrates an arbitrary sweep pattern for a pair of repeat sweeps is achieved by interleaving and changing the direction of the sweep.

In another embodiment one may choose to effectively sweep twice or multiple times before moving on to the next measurement location. As mentioned above, related concepts have been described in the prior art, where two consecutive sweeps have been compared to correct for motion artifacts (Hendargo et al., 2011). FIG. 7 illustrates the sweep patterns in time for two consecutive sweeps as used in the prior art. In slow sweeping systems, the time between two full sweeps of this type may however be too long. We therefore suggest interleaving two or more sweeps as illustrated in FIG. 8. Here, the overall frequency range is covered twice and the overall scan time is the same as two consecutive scans, but there is a reduced time between the repeated wavelength values. The interleaved sweeps may also be of arbitrary nature with increasing and decreasing spectral segments as illustrated in FIG. 9 and described above for individual sweeps. Instead of calculating for example the phase difference between two entire sweeps, one would calculate the phase difference between two corresponding segments.

Another related use of the above described interleaved scan modes is for OCT motion contrasting and quantification methods (OCT Angiography), including but not limited to Doppler OCT, phase variance or speckle variance techniques (see for example US Patent Publication Nos. 2005/0171438, 2012/0307014, 2010/0505127, 2012/0277579 and U.S. Pat. No. 6,549,801). By repeating part of the sweep twice or multiple times, instead of repeating the entire sweep twice or multiple times, one is able to reduce the time difference between measurements. The detectable velocity range correlates with the time difference between two measurements and is therefore adjustable by this method. Additionally one may also benefit from the advantages described in references (Jia et al., 2012; Sharma & Schmoll, 2013; Tokayer, Jia, Dhalla, & Huang, 2013).

Figure 10:
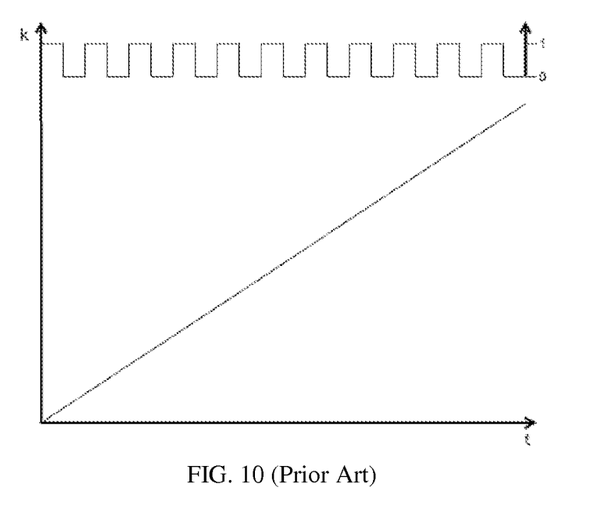
FIG. 10 illustrates a continuous sweep pattern of wavenumber vs. time as was shown in FIG. 1 and known in the Prior Art. The square signal at the top of the figure indicates the exposure time and dead time of the camera.
Figure 11:
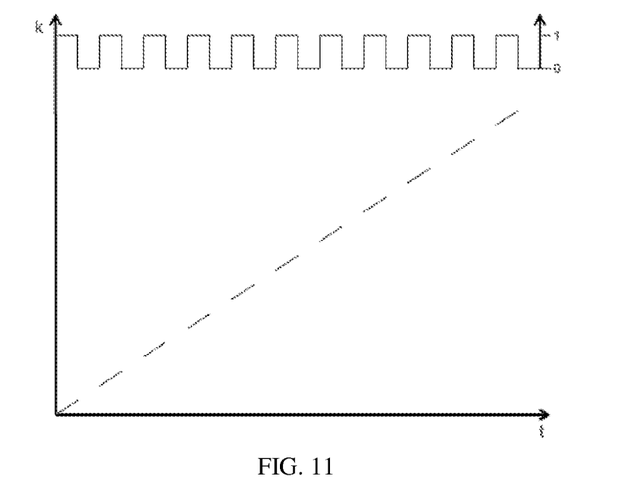
FIG. 11 illustrates a sweep pattern according to the present application in which the light output is synchronized to the dead time of the camera so light is not emitted during the dead time of the camera.

In another embodiment one may make use of the arbitrary sweep capability of certain swept source lasers to adapt the sweep trajectory, sweep speed, and output power to the detection of a swept source based interferometric imaging system. In particular, line field or full field based interferometric imaging systems typically employ 1D or 2D focal plane arrays as detectors in the system. These detectors often require a certain "dead time" in between exposures, during which the pixels are reset. During this time no light is converted into electrons by the camera, therefore all the light exposed to the sample during that time is lost. FIG. 10 illustrates a continuous sweep in wavenumber as in FIG. 2. The square signal trace at the top of the figure indicates the exposure time and dead time of the camera (1=exposure, 0=dead). The dead time of the camera is effectively ignored as is typically performed in SS-OCT systems in the prior art, and the laser outputs light during the entire course of the sweep. In order to avoid losing light it is desirable to switch off, or at least significantly reduce the laser output during the dead time of the camera. This concept is illustrated in FIG. 11 where the light output is synchronized to the duty cycle of the detector. No light is emitted between the dashed segments of the sweep.

Similar approaches have been previously presented for point scanning SD-OCT using a pulsed light source (Yun, Tearney, de Boer, & Bouma, 2004) and for line field SD-OCT using optical chopper wheels (Nakamura et al., 2007). So far it was however not feasible to implement a related concept for swept source based interferometric systems, because the swept sources used were not able to sufficiently quickly switch the laser output on and off many times during the course of a single sweep. In principle, one would be able to implement the above described concept also for swept source based interferometric systems with the use of optical choppers, but it is challenging to achieve sufficiently high chopping frequencies. Other methods to block the light during the camera dead time of a parallel swept source interferometric imaging system may be envisioned by persons skilled in the art.

Figure 12:
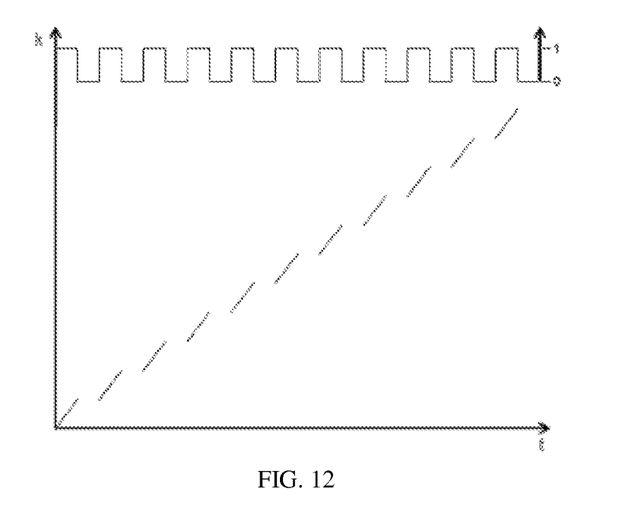
FIG. 12 illustrates a sweep pattern according to an embodiment of the present application in which the sweep rate is increased during the exposure time of the camera and the sweep is halted and the laser output is switched off during the dead time of the camera.
Figure 13:
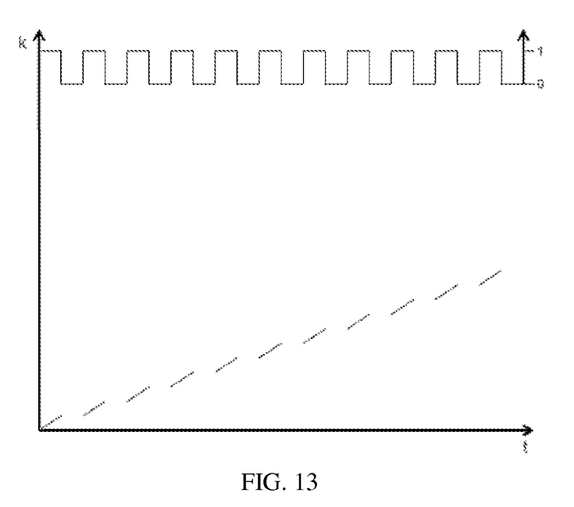
FIG. 13 shows a sweep pattern according to an embodiment of the present application where the sweep is halted and the laser output is switched off during the dead time of the camera.

To date published swept source line field and full-field OCT systems have swept continuously throughout the entire sweep (Bonin, Franke, Hagen-Eggert, Koch, & Huttmann, 2010; Hillmann, Franke, Luhrs, Koch, & Huttmann, 2012; Lee & Kim, 2008; Mujat et al., 2009; Povazay et al., 2006). (see FIG. 10). Such a sweep mode may be desirable in cases where spectral blurring is wanted. However, to improve the spectral sampling of the sweep it is proposed here to both increase the sweep rate during the camera exposure and halt the sweep during the dead time as illustrated in FIG. 12. Alternatively one could simply halt the sweep during the dead time of the camera as illustrated in FIG. 13. Since the sweep rate is not increased as in FIG. 12, the number of acquisitions per sweep has to be increased in order to sample the full sweep. Also in these cases it is of course desirable to switch off the laser output during the dead time as described above and illustrated in the figures by the gaps in the sweep which coincide with the camera dead time.

Figure 14:
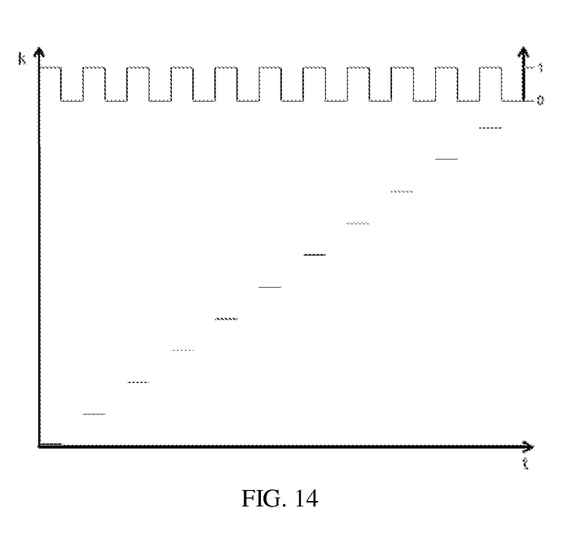
FIG. 14 illustrates a sweep pattern according to an embodiment of the present application where the source is swept stepwise over a range of wavenumbers over time. During the exposure time of the camera, the sweep is halted so only one wavenumber value is measured. The laser output is switched off during the camera dead time and moved to the next wavenumber step.

In another embodiment where one wants to minimize spectral blurring due to the integration of the camera throughout the exposure time it is advantageous to halt the sweep during the exposure time and use the dead time of the camera to move the laser output to the next wavelength or wavenumber bin, before the next camera exposure begins. The laser output would again ideally be switched off during the dead time of the camera. This concept is illustrated in FIG. 14.

Although various applications and embodiments that incorporate the teachings of the present invention have been shown and described in detail herein, those skilled in the art can readily devise other varied embodiments that still incorporate these teachings.

The following references are hereby incorporated by reference:

PATENT DOCUMENTS

U.S. Pat. No. 6,549,801
U.S. Pat. No. 8,973,066
US Publication No. 2005/0171438
US Publication No. 2012/0307014
US Publication No. 2010/0505127
US Publication No. 2012/0277579

NON-PATENT LITERATURE

Bonesi, M., Minneman, M. P., Ensher, J., Zabihian, B., Sattmann, H., Boschert, P., . . . Drexler, W. (2014). Akinetic all-semiconductor programmable swept-source at 1550 nm and 1310 nm with centimeters coherence length. *OPTICS EXPRESS*, 22(3), 2632. doi: 10.1364/oe.22.002632

Bonin, T., Franke, G., Hagen-Eggert, M., Koch, P., & Huttmann, G. (2010). In vivo Fourier-domain full-field OCT of the human retina with 1.5 million A-lines/s. *Opt Lett*, 35(20), 3432-3434. doi: 10.1364/OL.35.003432

Choi, D. H., Yoshimura, R., & Ohbayashi, K. (2013). Tuning of successively scanned two monolithic Vernier-tuned lasers and selective data sampling in optical comb swept source optical coherence tomography. *Biomed Opt Express*, 4(12), 2962-2987. doi: 10.1364/BOE.4.002962

Choma, M. A., Sarunic, M. V., Yang, C., & Izatt, J. A. (2003). Sensitivity advantage of swept source and Fourier domain optical coherence tomography. *OPTICS EXPRESS*, 11(18), 2183-2189.

George, B., & Derickson, D. (2010). High-speed concatenation of frequency ramps using sampled grating distributed Bragg reflector laser diode sources for OCT resolution enhancement. 7554, 755420-755420-75548. doi: 10.1117/12.842604

Hendargo, H. C., McNabb, R. P., Dhalla, A. H., Shepherd, N., & Izatt, J. A. (2011). Doppler velocity detection limitations in spectrometer-based versus swept-source optical coherence tomography. *Biomed Opt Express*, 2(8), 2175-2188. doi: 10.1364/BOE.2.002175

Hillman, D., Luhrs, C., Bonin, T., Koch, P., & Huttmann, G. (2011). Holoscopy-holographic optical coherence tomography. *Optics Letters*, 36(13), 2390-2392.

Hillmann, D., Franke, G., Luhrs, C., Koch, P., & Huttmann, G. (2012). Efficient holoscopy image reconstruction. *Opt Express*, 20(19), 21247-21263. doi: 10.1364/OE.20.021247

Huang, D., Swanson, E. A., Lin, C. P., Schuman, J. S., Stinson, W. G., Chang, W., . . . et al. (1991). Optical coherence tomography. *Science*, 254(5035), 1178-1181.

Ishii, H., Kano, F., Yoshikuni, Y., & Yasaka, H. (1998). Mode stabilization method for superstructure-grating DBR lasers. *Lightwave Technology, Journal of* 16(3), 433-442.

Ishii, H., Tanobe, H., Kano, F., Tohmori, Y., Kondo, Y., & Yoshikuni, Y. (1996). Quasicontinuous wavelength tuning in super-structure-grating (SSG) DBR lasers. *Quantum Electronics, IEEE Journal of* 32(3), 433-441.

Jia, Y., Tan, O., Tokayer, J., Potsaid, B., Wang, Y., Liu, J. J., . . . Huang, D. (2012). Split-spectrum amplitude-decorrelation angiography with optical coherence tomography. *Opt Express*, 20(4), 4710-4725. doi: 10.1364/OE.20.004710

Kim, M.-K. (2000). Tomographic three-dimensional imaging of a biological specimen using wavelength-scanning digital interference holography. *OPTICS EXPRESS*, 7(9), 305-310.

Lee, S.-W., & Kim, B.-M. (2008). Line-Field Optical Coherence Tomography Using Frequency-Sweeping Source. *IEEE Journal of Selected Topics in Quantum Electronics*, 14(1), 50-55. doi: 10.1109/jstqe.2007.914046

Leitgeb, R. A., Drexler, W., Unterhuber, A., Hermann, B., Bajraszewski, T., Le, T., . . . Fercher, A. F. (2004). Ultrahigh resolution Fourier domain optical coherence tomography. *OPTICS EXPRESS*, 12(10), 2156-2165.

Leitgeb, R. A., Hitzenberger, C. K., & Fercher, A. F. (2003). Performance of fourier domain vs. time domain optical coherence tomography. *OPTICS EXPRESS*, 11(8), 889-894.

Minneman, M. P., Ensher, J., Crawford, M., & Derickson, D. (2011). All-semiconductor high-speed akinetic swept-source for OCT. 8311, 831116. doi: 10.1117/12.912119

Mujat, M., Iftimia, N. V., Ferguson, R. D., & Hammer, D. X. (2009). *Swept-source parallel OCT*. Paper presented at the Optical Coherence Tomography and Coherence Domain Optical Methods in Biomedicine XIII.

Nakamura, Y., Makita, S., Yamanari, M., Itoh, M., Yatagai, T., & Yasuno, Y. (2007). High-speed three-dimensional human retinal imaging by line-field spectral domain optical coherence tomography. *OPTICS EXPRESS*, 15(12), 7103. doi: 10.1364/oe.15.007103

Povazay, B., Unterhuber, A., Hermann, B., Sattmann, H., Arthaber, H., & Drexler, W. (2006). Full-field time-encoded frequency-domain optical coherence tomography. *Opt Express,* 14(17), 7661-7669. doi: http://dx.doi.org/10.1364/OE.14.007661

Ralston, T. S., Marks, D. L., Scott Carney, P., & Boppart, S. A. (2007). Interferometric synthetic aperture microscopy. *Nature Physics,* 3(2), 129-134. doi: 10.1038/nphys514

Sharma, U., & Schmoll, T. (2013). Systems and methods for faster optical coherence tomography acquisition and processing: U.S. patent application Ser. No. 13/782,873.

Tokayer, J., Jia, Y., Dhalla, A. H., & Huang, D. (2013). Blood flow velocity quantification using split-spectrum amplitude-decorrelation angiography with optical coherence tomography. *Biomed Opt Express,* 4(10), 1909-1924. doi: 10.1364/BOE.4.001909

Yun, S. H., Tearney, G., de Boer, J., & Bouma, B. (2004). Pulsed-source and swept-source spectral-domain optical coherence tomography with reduced motion artifacts. *Opt Express,* 12(23), 5614-5624. doi: 10.1364/opex.12.005614

The invention claimed is:

1. A method for imaging a sample interferometrically comprising:
    illuminating the sample with a light source, said light source being swept over a range of frequencies;
    detecting combined light returning from the sample and light from a reference arm at a detector and generating signals in response thereto;
    processing said detected signals to generate an image of the sample,
    wherein the light source is swept with an arbitrary sweep pattern and wherein the arbitrary sweep pattern covers a continuous range of wavelengths and wherein the variation of wavelength over time is non-continuous.

2. An interferometric imaging method as recited in claim 1, wherein the light source illuminates a point on the sample.

3. An interferometric imaging method as recited in claim 1, wherein the light source illuminates a line on the sample.

4. An interferometric imaging method as recited in claim 1, wherein the light source illuminates a two dimensional area on the sample.

5. A method for imaging a sample interferometrically comprising:
    illuminating the sample with a light source, said light source being swept over a range of frequencies;
    detecting combined light returning from the sample and light from a reference arm at a detector and generating signals in response thereto, said detector having dead time between exposures; and
    processing said detected signals to generate an image of the sample wherein the light source is either turned off during the dead time of the detector or the output of the light source is reduced during the dead time of the detector.

6. A method as recited in claim 5, wherein the light source is swept using an arbitrary sweep pattern to cover a continuous range of wavelengths and wherein the variation of wavelength over time is non-continuous.

7. A method as recited in claim 5, wherein the sweeping of the light source is halted during the dead time of the detector.

8. A method as recited in claim 5, wherein the output of the light source is reduced during the dead time of the detector.

9. A method as recited in claim 5, wherein the output of the light source is turned off during the dead time of the detector.

* * * * *

UNITED STATES PATENT AND TRADEMARK OFFICE
CERTIFICATE OF CORRECTION

PATENT NO. : 9,778,018 B2
APPLICATION NO. : 14/613121
DATED : October 3, 2017
INVENTOR(S) : Tilman Schmoll et al.

It is certified that error appears in the above-identified patent and that said Letters Patent is hereby corrected as shown below:

In the Specification

In Column 5, Line 59, after "2011)" insert -- . --.

Signed and Sealed this
Twenty-seventh Day of March, 2018

Andrei Iancu
*Director of the United States Patent and Trademark Office*